(12) United States Patent
Al-Atat et al.

(10) Patent No.: US 10,024,465 B2
(45) Date of Patent: Jul. 17, 2018

(54) ENERGY HARVESTING CIRCUIT FOR LIFE-SENSING HOSE ASSEMBLY

(71) Applicant: EATON CORPORATION, Cleveland, OH (US)

(72) Inventors: Hassan Al-Atat, Chaska, MN (US); Pradeep Gokuldasji Bhutada, Maharashtra (IN); Nilesh Kailasrao Surase, Maharashtra (IN); James Dean Betsinger, Waterville, OH (US)

(73) Assignee: Eaton Intelligent Power Limited, Dublin (IE)

( * ) Notice: Subject to any disclaimer, the term of this patent is extended or adjusted under 35 U.S.C. 154(b) by 0 days.

(21) Appl. No.: 14/646,903

(22) PCT Filed: Mar. 13, 2013

(86) PCT No.: PCT/US2013/030966
§ 371 (c)(1),
(2) Date: May 22, 2015

(87) PCT Pub. No.: WO2014/081459
PCT Pub. Date: May 30, 2014

(65) Prior Publication Data
US 2015/0300538 A1    Oct. 22, 2015

(30) Foreign Application Priority Data
Nov. 22, 2012  (IN) .................................. 1346/2012

(51) Int. Cl.
*F16L 11/127*    (2006.01)
*G01M 3/18*      (2006.01)
(Continued)

(52) U.S. Cl.
CPC ............. *F16L 11/127* (2013.01); *F16L 25/01* (2013.01); *G01M 3/18* (2013.01); *G01M 5/00* (2013.01);
(Continued)

(58) Field of Classification Search
None
See application file for complete search history.

(56) References Cited

U.S. PATENT DOCUMENTS 2,291,070 A    7/1942    Bruno
2,436,949 A    3/1948    Anderson
(Continued)

FOREIGN PATENT DOCUMENTS

DE    31 40 804 A1    4/1983
DE    40 03 788 A1    8/1991
(Continued)

OTHER PUBLICATIONS

International Search Report and Written Opinion for Application No. PCT/US2011/061865 dated May 21, 2012.
(Continued)

*Primary Examiner* — Jermele M Hollington
*Assistant Examiner* — Douglas X Rodriguez
(74) *Attorney, Agent, or Firm* — Merchant & Gould P.C.

(57) ABSTRACT

A hose monitoring system and a method of monitoring a hose are disclosed. A system includes a hose assembly including a hose having a first conductive layer and a second conductive layer, and a monitoring circuit in electrical communication with the first and second conductive layers. The system also includes an energy harvesting unit in electrical communication with the monitoring circuit, the energy harvesting unit including one or more energy harvesters for providing electrical energy to the monitoring circuit.

20 Claims, 11 Drawing Sheets

(51) Int. Cl.
*G01M 5/00* (2006.01)
*F16L 25/01* (2006.01)
*G01N 27/02* (2006.01)
*H02J 7/00* (2006.01)
*H02J 7/34* (2006.01)

(52) U.S. Cl.
CPC ............ *G01N 27/02* (2013.01); *H02J 7/0042* (2013.01); *F16L 2201/30* (2013.01); *H02J 7/345* (2013.01)

(56) References Cited

U.S. PATENT DOCUMENTS

| | | |
|---|---|---|
| 2,451,450 A | 10/1948 | Spraragen |
| 4,029,889 A | 6/1977 | Mizuochi |
| 4,229,613 A | 10/1980 | Braun |
| 4,446,892 A | 5/1984 | Maxwell |
| 5,102,012 A | 4/1992 | Foster |
| 5,159,200 A | 10/1992 | Dunbar et al. |
| 5,267,670 A | 12/1993 | Foster |
| 5,343,738 A | 9/1994 | Skaggs |
| 5,387,899 A | 2/1995 | DiLauro et al. |
| 5,442,810 A | 8/1995 | Jenquin |
| 5,551,484 A | 9/1996 | Charboneau |
| 5,634,497 A | 6/1997 | Neto |
| 5,671,689 A | 9/1997 | Clapp et al. |
| 5,969,618 A | 10/1999 | Redmond |
| 5,992,218 A | 11/1999 | Tryba et al. |
| 6,384,611 B1 | 5/2002 | Wallace et al. |
| 6,386,237 B1 | 5/2002 | Chevalier et al. |
| 6,498,991 B1 | 12/2002 | Phelan et al. |
| 6,735,705 B1 | 5/2004 | Egbert et al. |
| 6,958,615 B2 | 10/2005 | Poulbot et al. |
| 7,555,936 B2 | 7/2009 | Deckard |
| 8,087,430 B1 | 1/2012 | Betz et al. |
| 8,183,872 B2 | 5/2012 | Stark |
| 8,217,669 B1 | 7/2012 | Watkins, Jr. |
| 8,515,687 B2 | 8/2013 | Pereira et al. |
| 8,829,929 B1 | 9/2014 | Watkins, Jr. |
| 8,997,792 B2 | 4/2015 | Betsinger et al. |
| 2001/0018845 A1 | 9/2001 | Roberts |
| 2002/0154029 A1 | 10/2002 | Watters et al. |
| 2003/0164048 A1 | 9/2003 | Shkel |
| 2004/0065377 A1 | 4/2004 | Whiteley |
| 2005/0253821 A1 | 11/2005 | Roeder |
| 2006/0196252 A1 | 9/2006 | Deckard |
| 2006/0196722 A1 | 9/2006 | Makabe et al. |
| 2006/0226701 A1 | 10/2006 | Gatz et al. |
| 2007/0051166 A1 | 3/2007 | Baker et al. |
| 2007/0131035 A1 | 6/2007 | Krutz et al. |
| 2008/0036617 A1 | 2/2008 | Arms et al. |
| 2009/0042419 A1 | 2/2009 | Palomo |
| 2010/0007325 A1* | 1/2010 | Stark ............. F16L 11/127 324/71.1 |
| 2010/0174495 A1 | 7/2010 | Pereira et al. |
| 2010/0308575 A1 | 12/2010 | Rodenburg |
| 2011/0152024 A1 | 6/2011 | Kuehl |
| 2011/0226302 A1 | 9/2011 | Fanner et al. |
| 2011/0281488 A1 | 11/2011 | Li |
| 2012/0032518 A1* | 2/2012 | Huang ............. H02J 1/10 307/81 |
| 2012/0136592 A1 | 5/2012 | Pereira et al. |
| 2012/0204923 A1* | 8/2012 | Ortiz ............. H01L 35/32 136/208 |
| 2012/0278018 A1 | 11/2012 | Hastreiter |
| 2013/0134992 A1 | 5/2013 | Zhu et al. |
| 2014/0076449 A1 | 3/2014 | Betsinger et al. |
| 2014/0238109 A1 | 8/2014 | Wells et al. |
| 2014/0265561 A1 | 9/2014 | Beining |
| 2015/0177172 A1 | 6/2015 | Upasani et al. |
| 2015/0240972 A1 | 8/2015 | Betsinger |

FOREIGN PATENT DOCUMENTS

| | | |
|---|---|---|
| EP | 1 126 205 A1 | 8/2001 |
| EP | 1 722 217 A1 | 11/2006 |
| EP | 2 261 546 A1 | 12/2010 |
| GB | 1574749 | 9/1980 |
| JP | 2011027216 | 2/2011 |
| WO | WO 03/079749 A2 | 10/2003 |
| WO | WO 2008/001238 A2 | 1/2008 |
| WO | WO 2008/059226 A2 | 5/2008 |
| WO | 2011/143384 | 11/2011 |
| WO | WO 2012/012482 A1 | 1/2012 |
| WO | WO 2012/071424 A2 | 5/2012 |
| WO | WO 2012/149161 A1 | 11/2012 |

OTHER PUBLICATIONS

International Search Report and Written Opinion for Application No. PCT/US2012/035216 dated Jul. 16, 2012.
International Search Report and Written Opinion for Application No. PCT/US2014/017590 dated Jun. 3, 2014.
International Search Report for Application No. PCT/IN2012/000296 dated Nov. 27, 2012.
Invitation to Pay Additional Fees with Partial International Search for Application No. PCT/US2013/048660 dated Mar. 24, 2014.
International Search Report and Written Opinion for Application No. PCT/US2013/048660 dated Sep. 8, 2014.
International Search Report for Application No. PCT/US2013/059465 dated Dec. 3, 2013.
Invitation to Pay Additional Fees with Partial International Search for Application No. PCT/US2013/059473 dated Feb. 28, 2014.
International Search Report and Written Opinion for Application No. PCT/US2013/059473 dated Jul. 18, 2014.
International Search Report and Written Opinion for Application No. PCT/US2014/029286 dated Jun. 18, 2014.
Hewlett Packard Technical Manual, printed Apr. 24, 2003, 8 Pages.
International Search Report for corresponding International Patent Application No. PCT/US2013/030966 dated Aug. 1, 2013.
Guo, Z. et al., "GRE: Graded Residual Energy Based Lifetime Prolonging Algorithm for Pipeline Monitoring Sensor", *9th International Conference on Parallel and Distributed Computing Applications and Technologies*, 203-210 (2008).
Mohamed, M. et al., "Power harvesting for smart sensor networks in monitoring water distribution system", *International Conference on Networking, Sensing and Control*, 393-398 (2011).
Ok, C. et al., "Optimal Transmission Power in Self-sustainable Sensor Networks for Pipeline Monitoring", *IEEE International Conference on Automation Science and Engineering*, 591-596 (2007).
Holland, Z. et al., "Layered Polymer Whole Structure Health Monitoring using Capacitance Sensing", *IEEE/ASME International Conference on Advanced intelligent Mechatronics*, 943-946 (2010).
Radtke, I. et al., "Design of Power-Transmitting Hydraulic Hose with Integrated Controller Area Network and Life-Sensing Capability", *American Society of Agricultural and Biological Engineers*, 1 page Abstract, (2005).
European Search Report for Application No. 12875245.8 dated Dec. 15, 2015.

* cited by examiner

ENERGY HARVESTING CIRCUIT FOR LIFE-SENSING HOSE ASSEMBLY

This application is a National Stage Application of PCT/US2013/030966, filed 13 Mar. 2013, which claims benefit of Indian Patent Application Serial No. 1346/KOL/2012 filed on 22 Nov. 2012 and which applications are incorporated herein by reference. To the extent appropriate, a claim of priority is made to each of the above disclosed applications.

TECHNICAL FIELD

The present application relates generally to a life-sensing hose assembly; in particular, the present application relates to an energy harvesting circuit for a life-sensing hose assembly.

BACKGROUND

High pressure reinforced hydraulic hose is typically used on a variety of fluid power operated machines, such as earth-moving machines, to provide a flexible connection between several moving parts of a hydraulic circuit employed on or within the machine. Such hoses may include a hollow polymeric inner tube on which successive cylindrical layers of reinforcing material, such as wire or textile, are concentrically applied to contain the radial and axial pressures developed within the inner tube.

Many applications are demanding hose constructions with both high burst strength and long term fatigue resistance. Using conventional technology, the burst strength of a hose design may be increased by adding additional reinforcing material and/or layers, a practice which is generally discouraged because of its negative impact on the flexibility of the hose, or by universally increasing the tensile strength of each layer of reinforcement material, which may come at the expense of hose fatigue resistance.

To determine the robustness of a hose design, a hose manufacturer typically performs, among other tests, an impulse test and a burst test on the hose. An impulse test measures a hose design's resistance to fatigue failure by cyclically subjecting the hose to hydraulic pressure. A burst test, on the other hand, is a destructive hydraulic test employed to determine the ultimate strength of a hose by uniformly increasing internal pressure until failure. Based on these and other tests, a manufacturer can estimate a hose life that can be used to determine when a hose has reached the end of its life and may require replacing.

In some circumstances, it is desirable to detect, in a non-destructive and non-disruptive manner a likelihood of failure of a hydraulic hose. One solution providing this capability is discussed in U.S. Pat. No. 7,555,936, and discloses connecting a monitor circuit between two parallel, at least partially-conductive layers of a hose wall. A change in an electrical property observed by that monitor circuit may indicate a change in a property of the hose wall structure that might indicate impending failure of the hose wall.

To determine whether changes in electrical properties of a hose assembly have occurred, an electrical circuit is applied to the conductive layers of the hose wall. The results of testing such an electrical property (e.g., resistance) can be stored and/or communicated by the electrical circuit to a monitor remote from that electrical circuit. For example, when used in the context of a fluid power operated machine, a monitor can be located in a cab or other area where an operator can readily assess status of such hoses.

Because industries are increasingly centralizing controls of hydraulic systems to meet customer requirements in terms of compactness, as well as ease of use and maintenance, the electrical circuits positioned on hoses positioned away from the cab will not have a convenient, directly wired source of power. Accordingly, the electrical circuits used to monitor hose degradation are typically battery-powered.

Battery-powered monitoring circuits have a number of challenges. For example, due to the need for a small-sized package, generally the battery to be used must have a small form factor (e.g., coin-sized, or AA-size or less). These batteries generally have limited life spans, particularly when exposed to extreme environmental conditions (e.g., −40 degree Fahrenheit temperatures). Additionally, using batteries in applications where a hydraulic hose is difficult to reach causes difficulties, because then battery changes and other maintenance tasks become difficult. Accordingly, it is desirable to reduce an amount of maintenance that would be required of a monitoring circuit.

For these and other reasons, improvements are desirable.

SUMMARY

In accordance with the following disclosure, the above and other issues are addressed by the following:

In a first aspect, a hose monitoring system is disclosed. A system includes a hose assembly including a hose having a first conductive layer and a second conductive layer, and a monitoring circuit in electrical communication with the first and second conductive layers. The system also includes an energy harvesting unit in electrical communication with the monitoring circuit, the energy harvesting unit including one or more energy harvesters for providing electrical energy to the monitoring circuit.

In a second aspect, a method of operating a hose monitoring system is disclosed. The method includes capturing energy via an energy harvesting unit associated with a hose assembly, the hose assembly including a hose having a first conductive layer and a second conductive layer. The method further includes providing the energy to a monitoring circuit in electrical communication with the first and second conductive layers. The method also includes, in response, assessing an electrical characteristic of the hose assembly via the monitoring circuit.

In a third aspect, a hose monitoring system includes a hose assembly including a hose having a first conductive layer and a second conductive layer, and a monitoring circuit in electrical communication with the first and second conductive layers. The system further includes an energy harvesting unit including a plurality of energy harvesters, and an energy booster circuit including an energy storage unit and a charge pump. The energy booster circuit is electrically connected between the energy harvesting unit and the monitoring circuit, and the charge pump is configured to enable storage of energy received from the energy harvesting unit in an energy storage unit. The energy storage unit is electrically connected to the monitoring circuit and providing power to the monitoring circuit.

In a fourth aspect, a hose assembly includes a hose and an energy harvesting unit. The energy harvesting unit includes a thermal energy harvester integrated with the hose to generate an electrical signal based on a temperature gradient across at least one layer of the hose.

DETAILED DESCRIPTION

Figure 1:
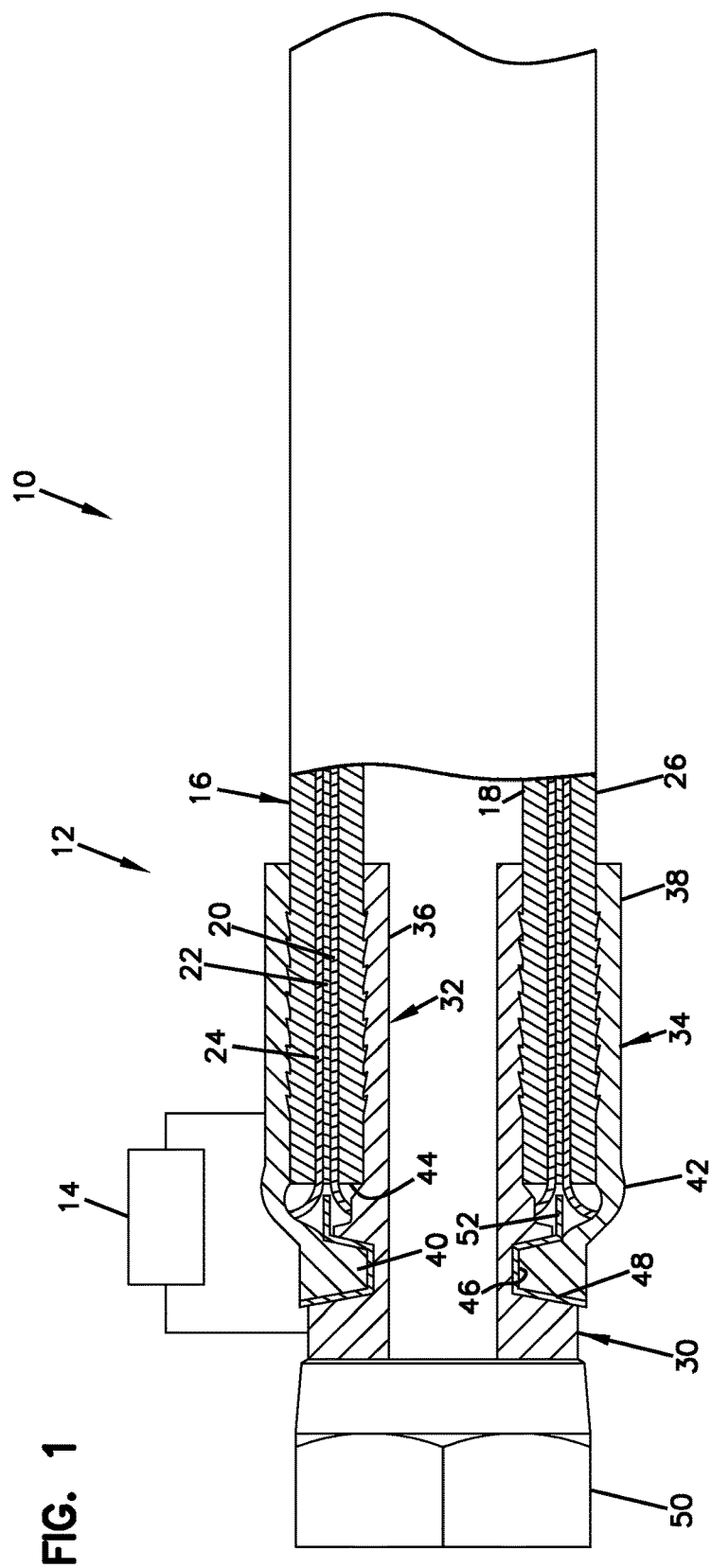
FIG. 1 is a partial cross-sectional view of an exemplary hose assembly employing a fault detector having exemplary features of aspects in accordance with the principles of the present disclosure.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

In general the present disclosure relates to a life-sensing hose assembly, and in particular, to an energy harvesting circuit for a life-sensing hose assembly. The energy harvesting circuit disclosed herein is configured to be interfaced to a monitoring circuit by an electrical booster circuit. Generally a charge pump can be selectively activated based on change applied to a battery or capacitor, and can activate use of an energy harvesting circuit to recharge the battery or capacitor. That battery or capacitor can then be used to provide power to a monitoring and communication circuit, so that the monitoring and communication portions of that circuit can determine an electrical characteristic of a hose assembly and communicate that information to a remote system.

As discussed herein, reference will now be made in detail to the exemplary aspects of the present disclosure that are illustrated in the accompanying drawings. Wherever possible, the same reference numbers will be used throughout the drawings to refer to the same or like structure.

Referring now to FIG. 1, an exemplary hose fault detection system, generally designated 10, is shown. The hose fault detection system 10 includes a hose assembly, generally designated 12, and a monitoring assembly 14 in electrical and physical communication with the hose assembly 12.

The hose assembly 12 includes a hose, generally designated 16, having a multi-layer construction. In the subject embodiment, the hose 16 is generally flexible and includes an inner tube 18 made from a polymeric material, such as rubber or plastic, or another material depending on the requirements of the particular application, a first conductive layer 20, an intermediate layer 22, a second conductive layer 24 and an outer cover 26. The first and second conductive layers 20, 24 define an electrical characteristic of the hose assembly 12, such as capacitance, inductance and/or resistance (impedance).

In the subject embodiment, the first conductive layer 20 overlays the inner tube 18 and the intermediate layer 22 overlays the first conductive layer 20. The second conductive layer 24 overlays the intermediate layer 22. The first and second conductive layers 20, 24 may be configured as reinforcing layers. The outer cover 26 may overlay the second conductive layer 24, and may include, for example, an extruded layer of rubber or plastic. The outer cover 26 may itself include a reinforcing layer.

The intermediate layer 22 operates to at least partially insulate electrically the first and second conductive layers 20, 24 from one another. The intermediate layer 22 may have any of a variety of constructions. For example, the intermediate layer 22 may consist of a single layer of an electrically resistive material. The intermediate layer 22 may also consist of multiple layers, wherein at least one of the layers exhibits electrical insulating properties. Certain composite materials may also be employed in the intermediate layer 22, such as a woven fabric bonded to a polymeric material. Composite materials having various other constructions may also be utilized. Composite materials may also be used in combination with other materials to form the intermediate layer 22.

The first and second conductive layers 20, 24 generally extend the entire length and span the entire circumference of the hose. This is generally the case when the conductive layer also functions as a reinforcement layer. The intermediate layer 22 may also extend over the entire length and circumference of the hose. There may be instances, however, where at least one of the first and second conductive layers 20, 24 extends only over a portion of the hose length and/or a portion of its circumference. In that instance, the intermediate layer 22 may also be configured to generally extend over the region of the hose containing the partial conductive layer 20, 24. The partial intermediate layer 22 may be positioned within the hose so as to separate the first and second conductive layers 20, 24 from one another.

Figure 2:
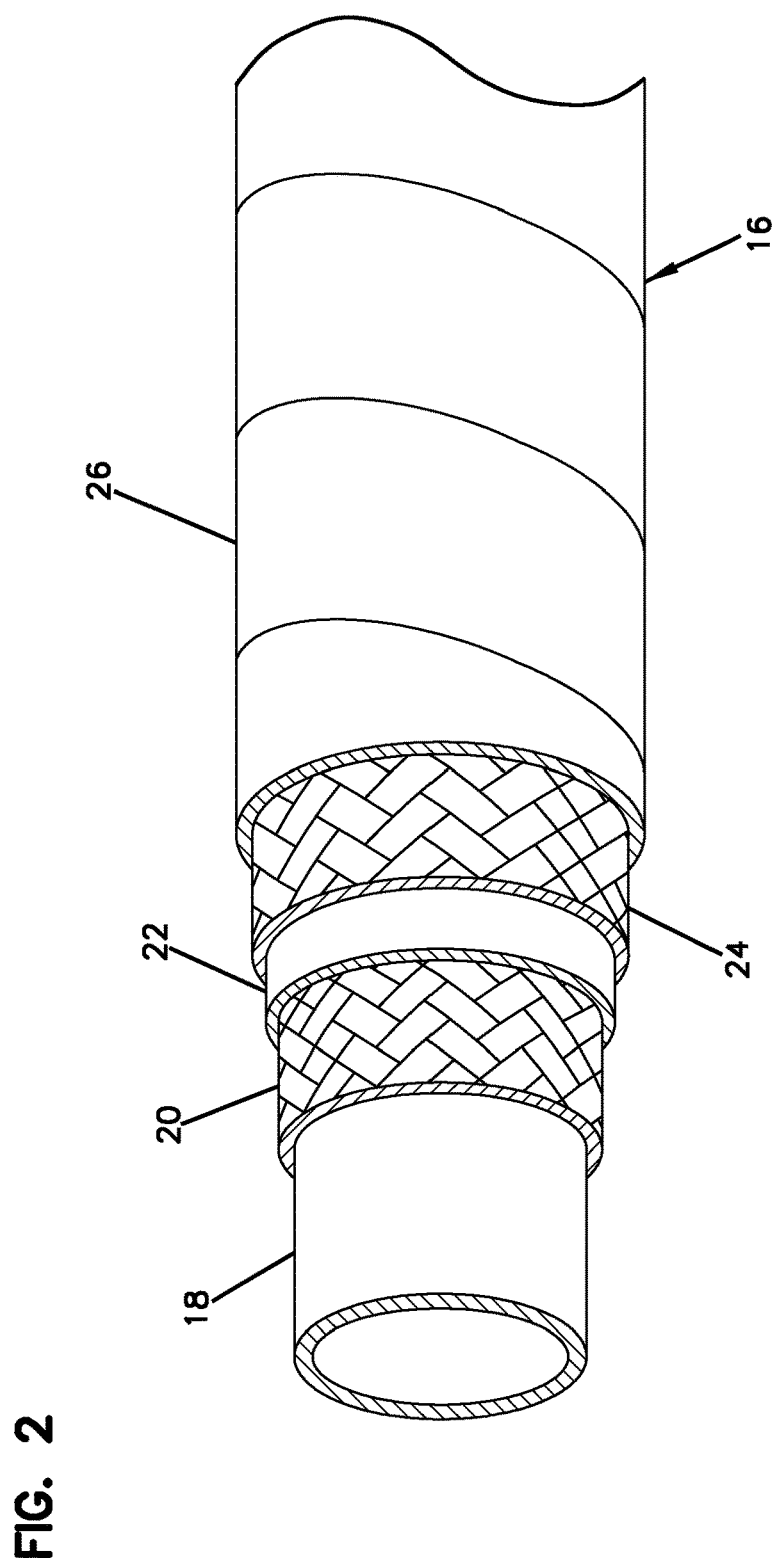
FIG. 2 is a perspective view, partially cut away, illustrating an exemplary hose employing a braided conductive layer that is suitable for use with the hose assembly of FIG. 1.
Figure 3:
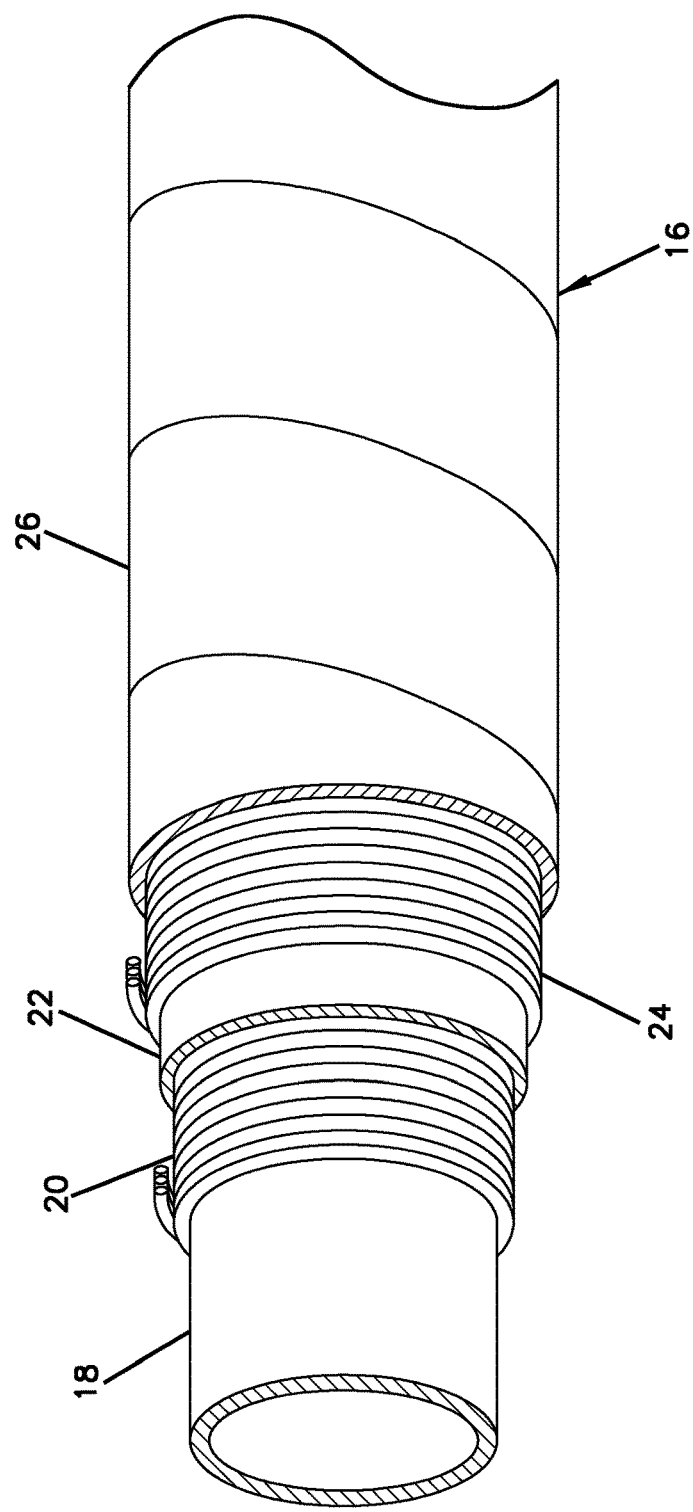
FIG. 3 is a perspective view, partially cut away, illustrating an exemplary hose employing a spiral wire conducting layer that is suitable for use with the hose assembly of FIG. 1.

Referring now to FIGS. 2 and 3, the first and second conductive layers 20, 24 may include, for example, an electrically conductive braided reinforcement material, such as shown in FIG. 2, or alternating layers of electrically conductive spiral reinforcement material, such as shown in FIG. 3. The braided reinforcement material may consist of a single layer or may include multiple layers. Although a two-wire spiral reinforcement arrangement is depicted in FIG. 3, it shall also be appreciated that other configurations, such as four and six wire arrangements, may also be utilized.

The first and second conductive layers 20, 24 may each have the same configuration, or each layer may be configured differently. For example, the first and second conductive layers 20, 24 may each include the braided material shown in FIG. 2, or one of the first and second conductive layers 20, 24 may include the braided material while the other of the first and second conductive layers 20, 24 may include the spiral reinforcement material shown in FIG. 3. Additionally, the first and second conductive layers 20, 24 may include a single ply or multiple plies of reinforcement material. The first and second conductive layers 20, 24 may comprise metal wire, natural or synthetic fibers and textiles, and other reinforcement materials, provided the selected material is electrically conductive.

Referring again to FIG. 1, the hose assembly 12 may include a hose fitting, generally designated 30, for fluidly coupling the hose 16 to another component. The hose fitting 30 may have any of a variety of different configurations depending, at least in part, on the requirements of the particular application.

In the subject embodiment, the hose fitting 30 includes a nipple, generally designated 32, that engages the inside of the hose 16 and a socket, generally designated 34, that engages the outside of the hose 16. The nipple 32 includes an elongated cylindrical end portion 36 that engages the inner tube 18 of the hose 16. A cylindrically shaped end portion 38 of the socket 34 engages the outer cover of the hose 16. The socket 34 and nipple 32 may be constructed from an electrically conductive material.

The socket 34 and nipple 32 can be secured to the hose 16 by crimping the end portion 38 of the socket 34 overlaying the hose 16. The crimping process deforms the end portion 38 of the socket 34, thereby compressing the hose 16 between the nipple 32 and the socket 34. In the subject embodiment, the portions of the nipple 32 and the socket 34 that engage the hose 16 include a series of serrations that at least partially embed into the relatively softer hose material when the socket 34 is crimped to help secure the hose fitting 30 to the hose 16. The serrations may be configured to prevent the serrations from penetrating the inner tube and outer cover and contacting the first and second conductive layers 20, 24.

In the subject embodiment, the socket 34 includes an inwardly extending circumferential lug 40 positioned near an end 42 of the socket 34 adjacent an end 44 of the hose 16. The lug 40 engages a corresponding circumferential slot 46 formed in the nipple 32 for securing the socket 34 to the nipple 32. The end 42 of the socket 34 having the lug 40 is initially formed larger than the nipple 32 to enable the socket 34 to be assembled onto the nipple 32. During the assembly process the end 42 of the socket 34 is crimped, which deforms the socket 34 and forces the lug 40 into engagement with the corresponding slot 46 in the nipple 32. The socket 34 can be electrically insulated from the nipple 32 by positioning an electrically insulating collar 48 between the socket 34 and nipple 32 at the point the lug 40 engages the slot 46.

The hose fitting 30 also includes a nut 50 rotatably attached to the nipple 32. The nut 50 provides a means for securing the hose assembly 12 to another component.

The first conductive layer 20 may be configured to extend beyond the end of the inner tube of the hose 16. The first conductive layer 20 may engage the nipple 32 to create an electrical connection between the nipple 32 and the first conductive layer 20. Similarly, the second conductive layer 24 may be configured to extend beyond an end of the outer cover of the hose 16. The second conductive layer 24 may engage the socket 34 to create an electrical connection between the socket 34 and the second conductive layer 24.

To help prevent the portions of the first and second conductive layers 20, 24 that extend beyond the end of the hose 16 from contacting one another, an electrically insulating spacer 52 may be positioned between the exposed ends of the first and second conductive layers 20, 24. The spacer 52 may be integrally formed as part of the collar 48 used to electrically insulate the socket 34 from the nipple 32. The spacer 52 may also be formed by extending the intermediate layer 22 of the hose 16 beyond an end of the inner tube 18 and outer cover 26. The spacer 52 may also be configured as a stand alone component separate from the collar 48 and the intermediate layer 22 of the hose 16.

The monitoring assembly 14 may have any of a variety of configurations. In general, the monitoring assembly 14 is connectable over a portion of the hose assembly 12, in particular the portion illustrated in FIG. 1. The monitoring assembly 14, when installed over hose assembly 12, forms a physical and electrical connection with the hose assembly 12, and in particular to nipple 32 and socket 34, respectively. Generally, the monitoring assembly 14 detects an electrical characteristic of the hose assembly 12, while validating the connection to the nipple 32 and socket 34. Example monitoring assemblies are disclosed in copending U.S. patent application Ser. No. 13/458,691, entitled "Degradation Monitoring System for Hose Assembly", and U.S. Provisional Patent Application No. 61/701,325 entitled "Sense and Hold Circuit for Hose Assembly", the disclosures of which are hereby incorporated by reference in their entireties.

Figure 4:
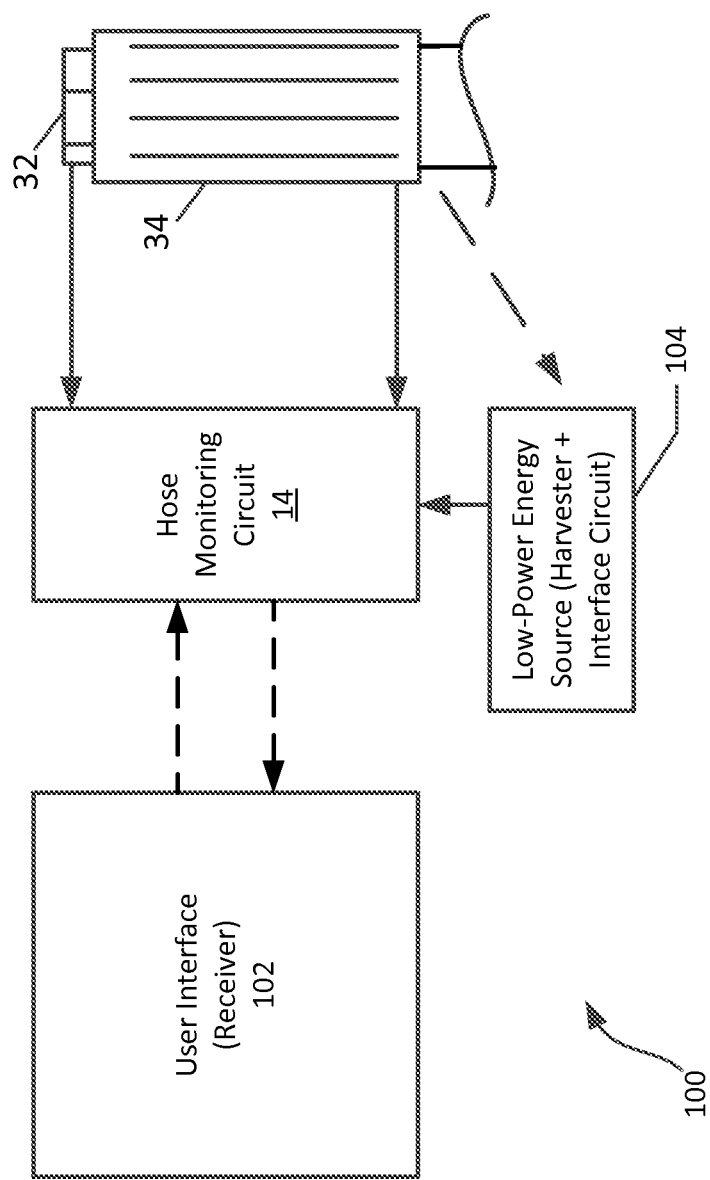
FIG. 4 is a schematic view of a hose monitoring system incorporating a hose assembly as illustrated in FIG. 1.

Referring now to FIGS. 4-10, generally methods and systems for monitoring a hose assembly 12, as well as methods for powering such monitoring circuitry that monitors the hose assembly, are disclosed. Generally, FIG. 4 illustrates a general concept of using an energy harvesting unit in association with a monitoring circuit, while FIGS. 5A-5D illustrate example energy harvesting units that could be used in connection with the monitoring assembly. FIGS. 6-11 illustrate example circuits that can be integrated with a monitoring assembly in association with a hose assembly 12, and methods of operation of those circuits to provide power to a monitoring circuit.

Referring now to FIG. 4, a schematic view of a hose monitoring system 100 is shown, incorporating a hose assembly 12 as illustrated in FIG. 1. The example embodiment shown specifically illustrates the nipple 32 and socket 34 of the end of the hose assembly 12, in that they are schematically electrically connected to monitoring circuit 14.

In the embodiment shown, the system 100 includes a receiver 102, also referred to as a remote user interface, which allows for centralized monitoring of one or more hose assemblies via communicative connection to the monitoring circuit 14. In example embodiments, the receiver 102 provides at least a visual indicator (e.g., LED) of a status of a hose assembly; in some embodiments, a web interface is provided that allows for interactive monitoring of all hose assemblies in an aggregated system. In example embodiments, the communicative connection between the monitoring circuit 14 and the receiver 102 is a wireless connection; however, in other embodiments, other types of communicative connections could be used as well.

In the embodiment shown, the system 100 further includes an energy source 104 used to provide power to the monitoring circuit, to support monitoring of the hose assembly and communication with the receiver. In example embodiments discussed in further detail below, the energy source 104 includes an energy harvesting unit and an energy boosting unit. As discussed in further detail below, the energy harvesting unit is configured to collect energy from one or more sources (e.g., as illustrated in FIGS. 5A-5D, below), while the energy boosting unit collects the harvested energy and, as appropriate, delivers that energy to the monitoring circuit. Details regarding the energy harvesting unit are discussed below in connection with FIGS. 6-8; details regarding the energy boosting unit are described below in connection with FIGS. 9-11.

Figure 5A:
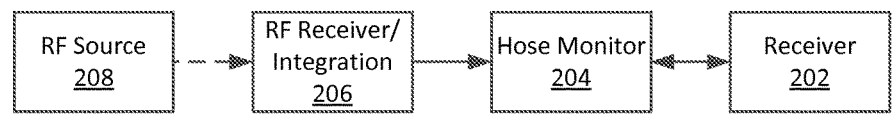
FIG. 5A is a schematic illustration of an RF energy harvesting arrangement, according to an example embodiment.

Referring now to FIGS. 5A-5D, various arrangements are illustrated for energy harvesting, as applied within the context of a hose assembly as illustrated in FIG. 1, above. In FIG. 5A, a first arrangement 200 is illustrated in which a receiver 202 is communicatively connected to a monitor circuit 204. These components generally correspond to components 102 and 14 of FIG. 4. In FIG. 5A, a wireless harvesting arrangement is disclosed that harvests energy from radio frequency signals that are present in the vicinity of the hose assembly 12. In the embodiment shown, an RF receiver 206 is integrated with the hose and monitor circuit 204, and receives RF signals from an RF source 208, which could be located remotely from the RF receiver (e.g., at a cab of a vehicle using a fluid hose implementing hose assembly 12). The RF receiver 206 includes an energy harvester, such that RF signals are converted to electrical impulses that can be aggregated in a capacitor or other electrical storage device, such as a battery. As discussed below, once the energy storage device voltage reaches a sufficient energy level, it triggers the monitoring circuit 204, which in turn senses hose characteristics, and transmits data to the receiver 202.

Figure 5B:
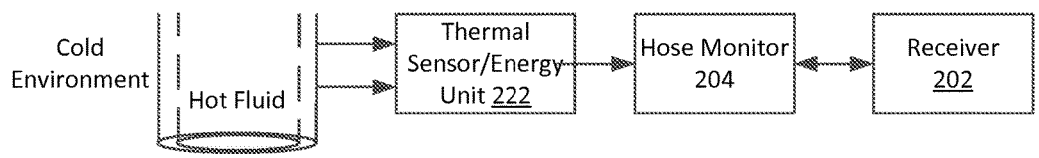
FIG. 5B is a schematic illustration of a thermal energy harvesting arrangement, according to an example embodiment.

FIG. 5B illustrates a second arrangement 220 that includes a thermal energy harvesting unit is shown. In this arrangement, a thermal sensor 222 can be applied to monitor a temperature gradient within the hose assembly 12. Generally, the thermal sensor can be used because the hose 12 generally carries fluids that operate at a higher temperature than a surrounding environment. The thermal gradient can be harnessed to generate energy.

Figure 5C:
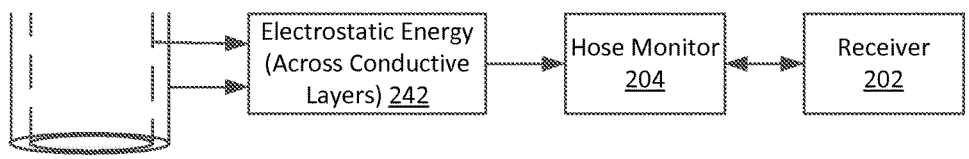
FIG. 5C is a schematic illustration of an electrostatic energy harvesting arrangement, according to an example embodiment.

FIG. 5C shows a third arrangement 240 that includes an electrostatic energy harvesting arrangement. In the embodiment shown, an electrostatic energy harvesting unit 242 collects static charges developed in hose due to impulse pressure, which can be utilized to generate power to excite the monitor circuit.

Figure 5D:
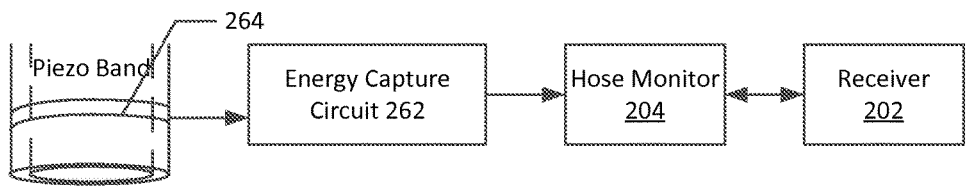
FIG. 5D is a schematic illustration of a piezoelectric energy harvesting arrangement, according to an example embodiment.

FIG. 5D shows a fourth arrangement 260 that includes a piezoelectric energy harvesting arrangement. The arrangement 260 includes a piezoelectric harvesting unit 262, and a piezo band 264 applied to the hose assembly. As the hose expands and contracts due to a hydraulic fluid pressure cycle, the piezo band 264 will be stressed, resulting in an electrical signal that can be captured by the harvesting unit 262.

In addition to the energy harvesting arrangements of FIGS. 5A-5D, other types of energy harvesting arrangements are possible as well. For example, a vibrational energy harvesting arrangement could be used as well, which could be implemented analogously to the piezoelectric energy harvester in arrangement 260.

Figure 6:
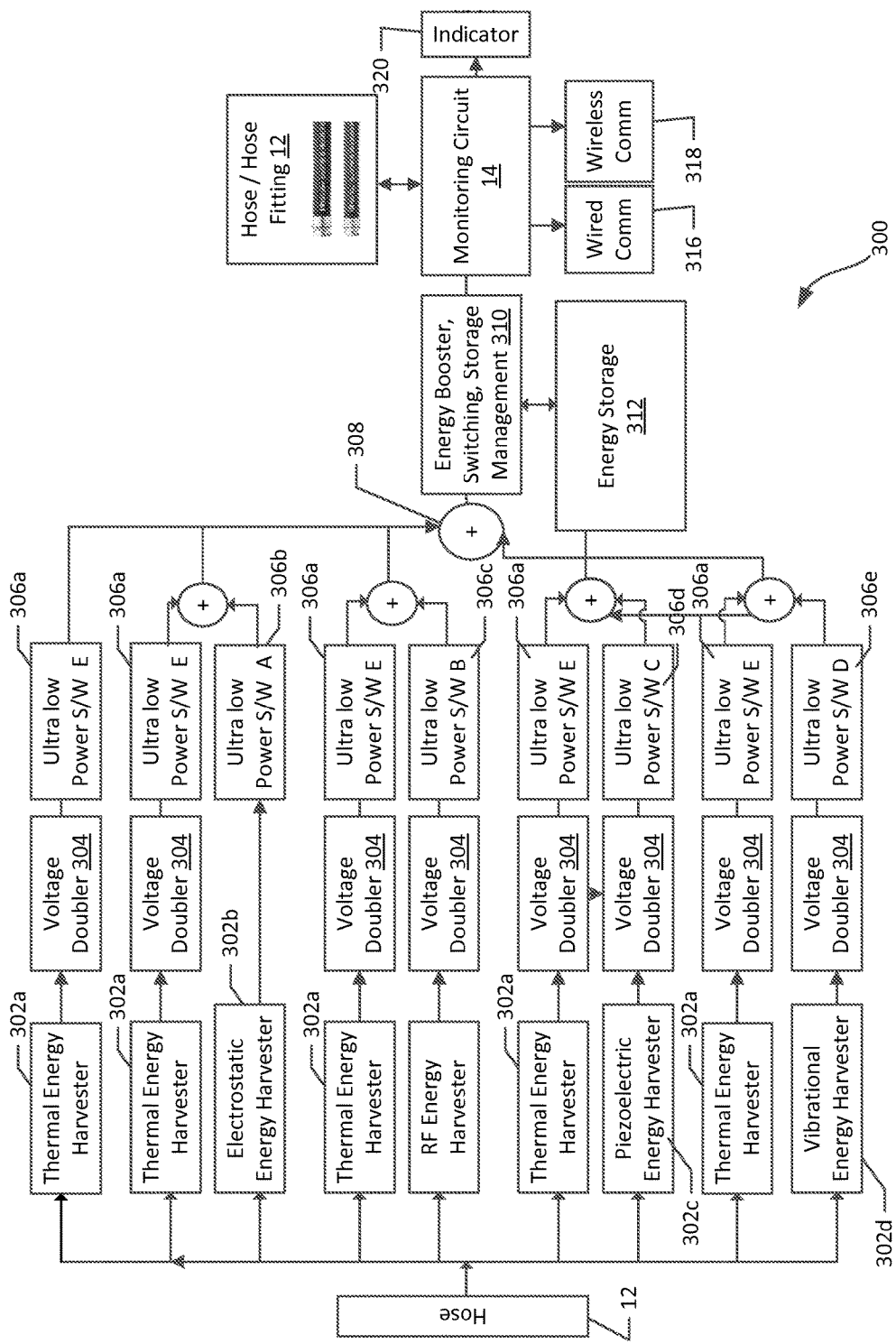
FIG. 6 is a schematic block diagram illustrating an energy harvesting arrangement useable in connection with a hose assembly such as that shown in FIG. 1, according to an example embodiment.

Referring now to FIG. 6, a schematic block diagram of an overall energy harvesting arrangement 300 that can be used as an energy harvesting unit is shown. The energy harvesting arrangement includes a plurality of energy harvesters 302a-e that can be integrated with a hose assembly 12. It is noted that each of the energy harvesters can have a voltage doubler circuit 304 associated therewith, other than electrostatic harvester 302b due to the pulsed nature of that energy harvesting arrangement. A low-power switch 306a-e, each associated with each type of energy harvester, can also be included in series with each energy harvester, and is used to select the type of particular harvester combination to be applied. As illustrated, each low power switch can be implemented as a zero-biased Schottky diode used to turn on at a low-power signal, and output to a summation unit 308. As illustrated, the low-power switches 306 are separated by type, to allow for selection of each different type of energy harvester independently of the other energy harvesters.

From the various energy harvesters 302, energy is summed and passed to an energy booster unit 310. The energy booster unit 310 manages energy storage in an energy storage unit 312, which collects harvested energy from the energy harvesters 302. The energy can then be passed by the energy booster unit 310 to a monitoring circuit 14. The monitoring circuit 14 provides an interface to one or both of a wired communication interface 316, or a wireless communication interface 318. In some embodiments, only the wireless communication interface 318 is provided.

Furthermore, in some embodiments, the monitoring circuit 14 is electrically connected to an indicator 320, which can be arranged to provide a visual indication of a state of the hose assembly 12. In some embodiments, the indicator 320 can correspond to an LED or other light indicator. In still further embodiments, the indicator 320 may be used in place of the wired communication interface and/or wireless communication interface 318, with the communication interfaces 316, 318 removed entirely.

Figure 7:
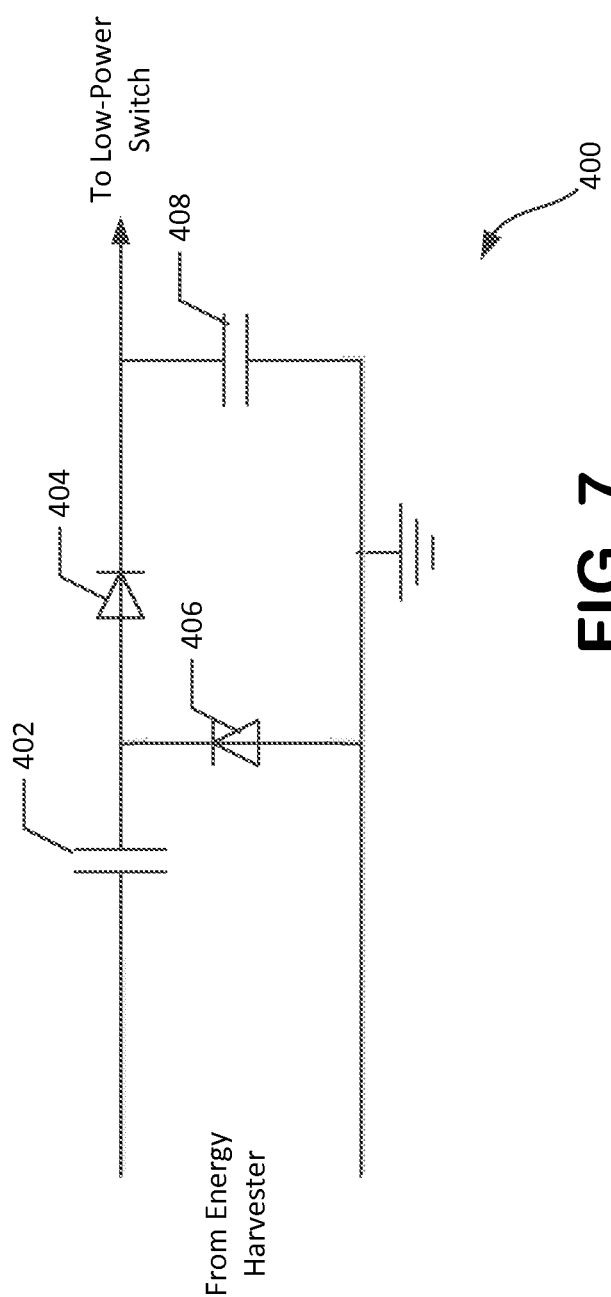
FIG. 7 illustrates a voltage doubler circuit useable in the energy harvesting arrangement of FIG. 6.

Referring now to FIG. 7, a voltage doubler circuit 400 is illustrated that can be used, for example, as voltage doubler 304 of FIG. 6. The voltage doubler circuit includes a capacitor 402 and signal diodes 404, 406 connected back to back. During a negative voltage half cycle of harvester output, diode 406 is forward biased, and a charge from capacitor 402 becomes a series arrangement with the harvester, thereby causing output voltage to diode 404. Diode 404 then turns "on" and energy output is created. Capacitor 408 stores energy and maintains a voltage level on the output path.

Figure 8:
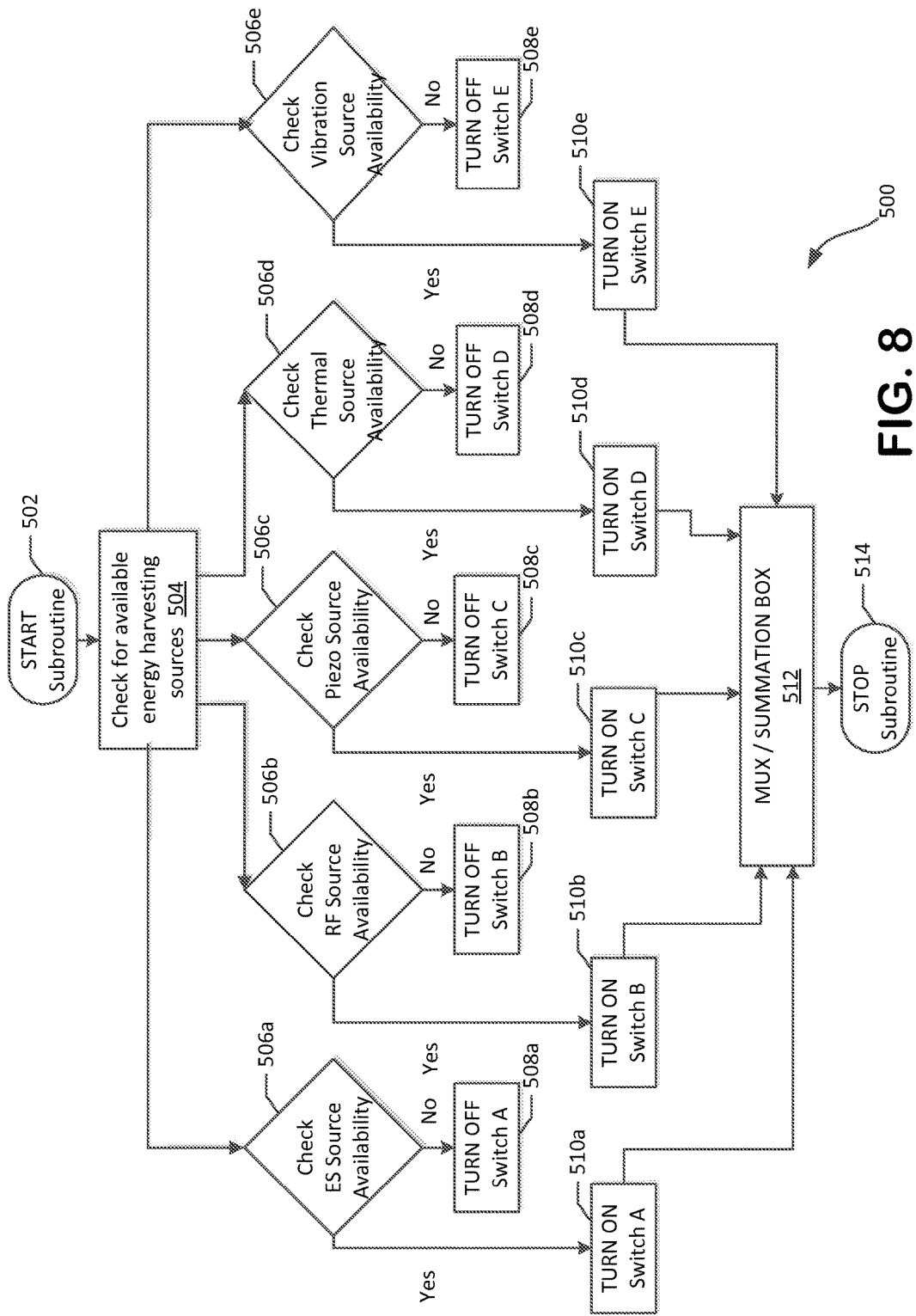
FIG. 8 is a flowchart of a method for harvesting energy from a plurality of energy sources for use in a hose assembly as discussed herein, according to a possible embodiment.

Referring to FIG. 8, a flowchart of a method 500 for harvesting energy from a plurality of energy sources for use in a hose assembly is illustrated. The method 500 is instantiated at a start operation 502, and proceeds to determine whether any of a variety of types of energy harvesters are available from which to receive energy (step 504). For each of the available energy harvester types, a check is performed to determine whether the source of energy is available (steps 506a-e). If the source of energy is not available, a switch (e.g., low power switch 306) connecting to that energy harvester is deactivated (steps 508a-e). However, if the source of energy is available, the switch 306a-e for that type of harvester is activated to allow for collection of energy from that source (step 510a-e).

Figure 9:
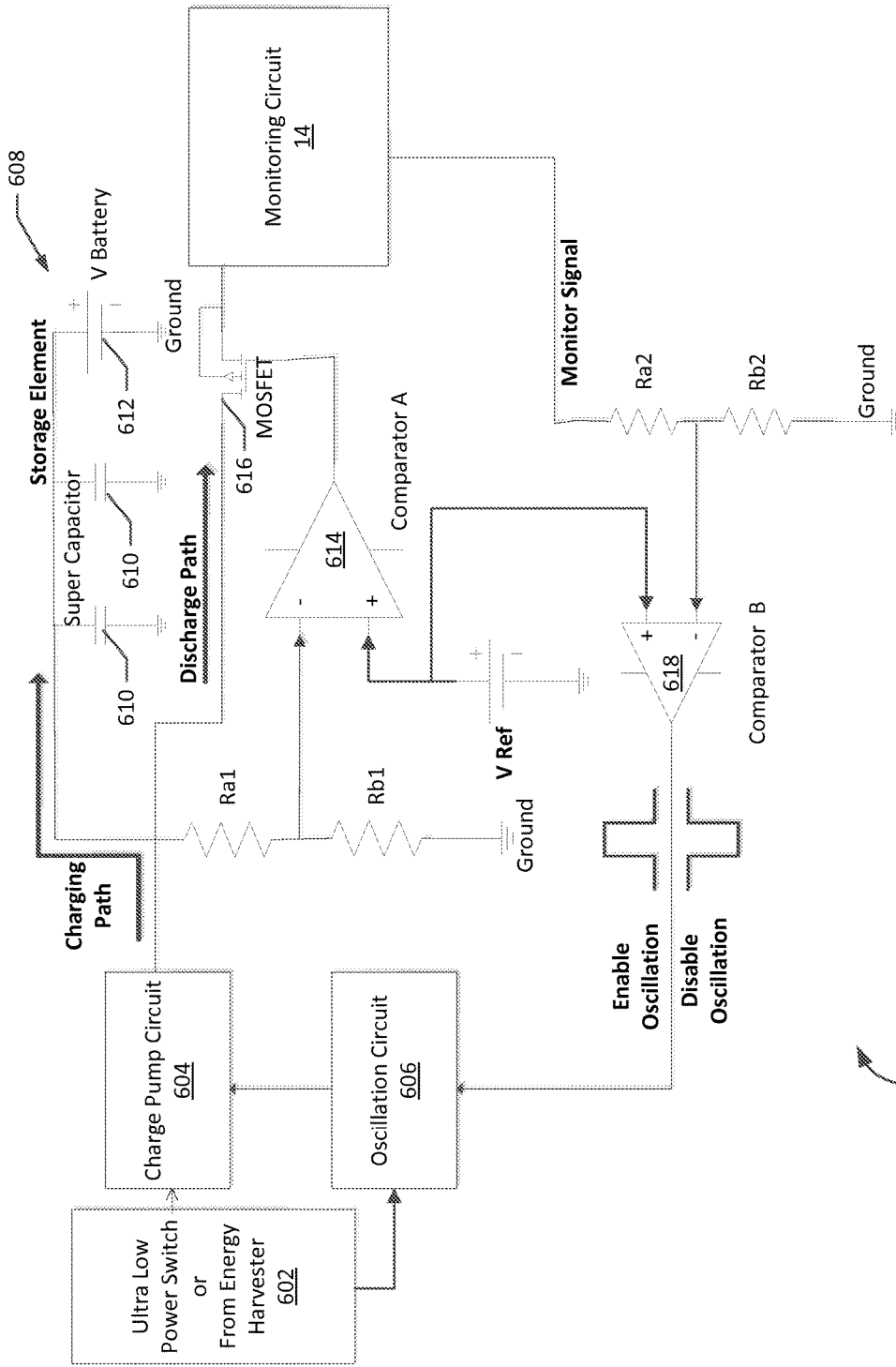
FIG. 9 is a schematic block diagram of an energy booster circuit configured to interface to the energy harvesting arrangement of FIG. 6.

A summation operation 512 collects energy from each of the types of energy harvesters, for storage using the energy booster unit 310 and associated energy storage unit 312 of FIG. 9. Operational flow within the overall method 500 terminates at end operation 514.

Referring now to FIG. 8, a schematic block diagram of an energy booster circuit 600 is shown, according to a possible embodiment of the present disclosure. The energy booster circuit 600 represents, for example one embodiment of the energy booster unit 310 and energy storage unit 312 of FIG. 6.

The energy booster circuit 600 receives energy from a summation of low power switches (shown as unit 602), and passes energy to a charge pump circuit 604 and an oscillation circuit 606. The charge pump circuit 604 generally includes a plurality of micro power step-up low voltage boosters, and acts to convert a low direct current DC voltage input to a higher alternating or direct current output. The charge pump circuit can also include a local capacitor to storage energy for temporary basis. Those capacitors are connected to input of oscillation circuit 606. In some embodiments, the oscillation circuit 606 includes an integrated ring oscillator circuit.

A very low voltage generated in each of the harvesters in will be amplified by the charge pump circuit as assisted by the oscillation circuit 606, depending on the current energy storage level in a storage unit 608. In the embodiment shown the storage unit 608 includes a plurality of high capacity capacitors 610, and a battery 612; however in various embodiments, different ones of these storage elements could be used. For example a lead acid battery, thin film battery, or super capacitor could be used.

In some embodiments, due to use of various types of energy harvesters, it may be possible to remove a battery altogether from the circuit, thereby relying solely on capacitor charge to power the circuit. In this way, concerns regarding battery life in hose assemblies located in inconvenient or dangerous locations can largely be alleviated.

Within the circuit, when the energy level of the storage unit 608 is sufficiently high, a first comparator 612 enables activation of the monitoring circuit 14 by activating MOSFET switch 616. This allows the monitoring circuit 14 to detect a particular electrical characteristic of a hose assembly and communicate that characteristic to a remote system. Furthermore, if the storage unit 608 includes a charge level that is sufficiently high, the energy harvesting unit will be disabled by a second comparator 618.

If the voltage level in the storage unit 608 is below a reference signal 620, comparator 612 causes MOSFET switch 616 to disconnect the storage unit 608 from the monitoring circuit 14. If a monitor signal from the monitoring circuit 14 is below the reference signal at comparator 618, that comparator activates the oscillation circuit 606, enabling recharging of the storage unit 608.

Figure 10:
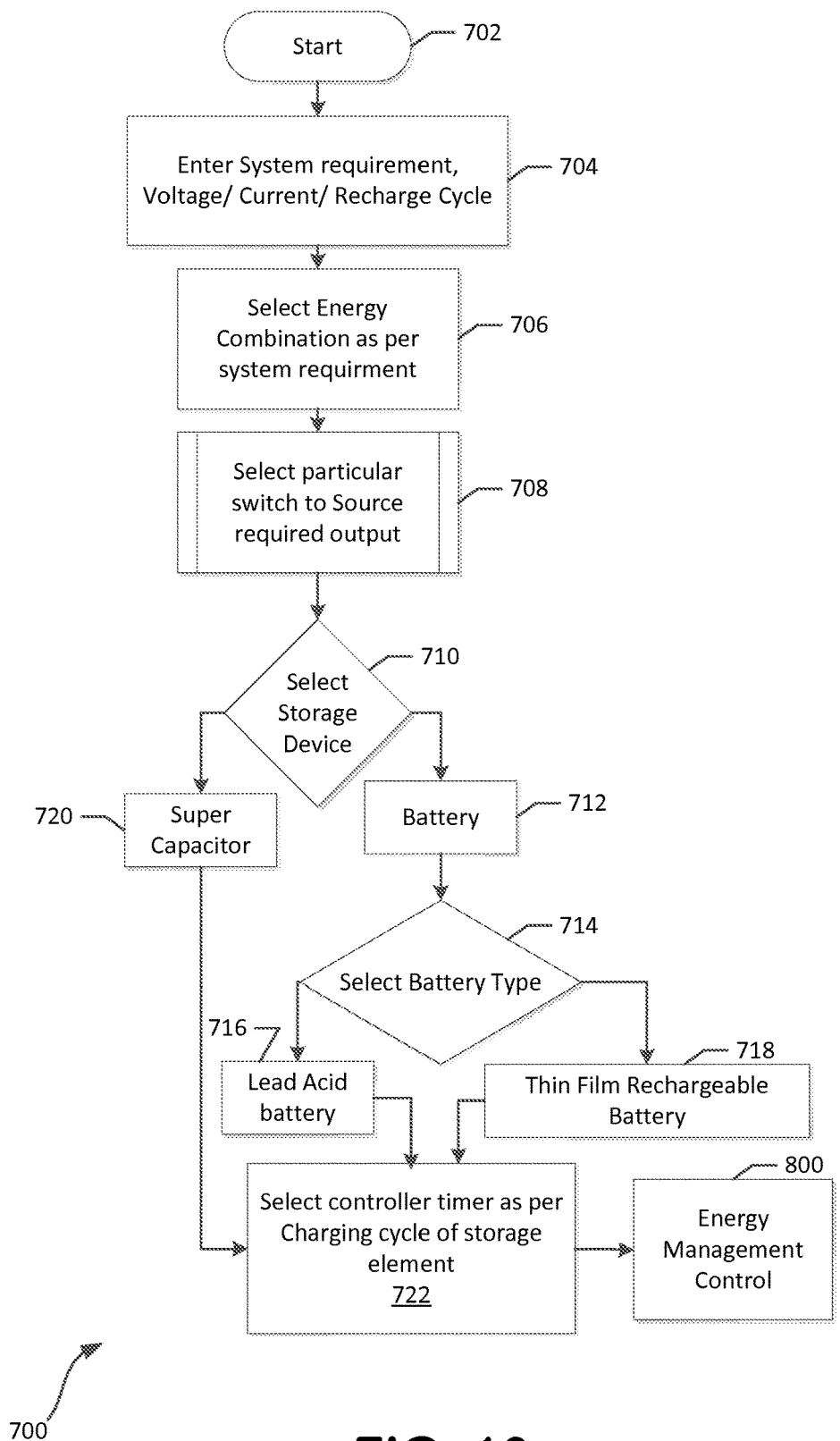
FIG. 10 is a flowchart of a method for configuring the energy booster circuit of FIG. 9.
Figure 11:
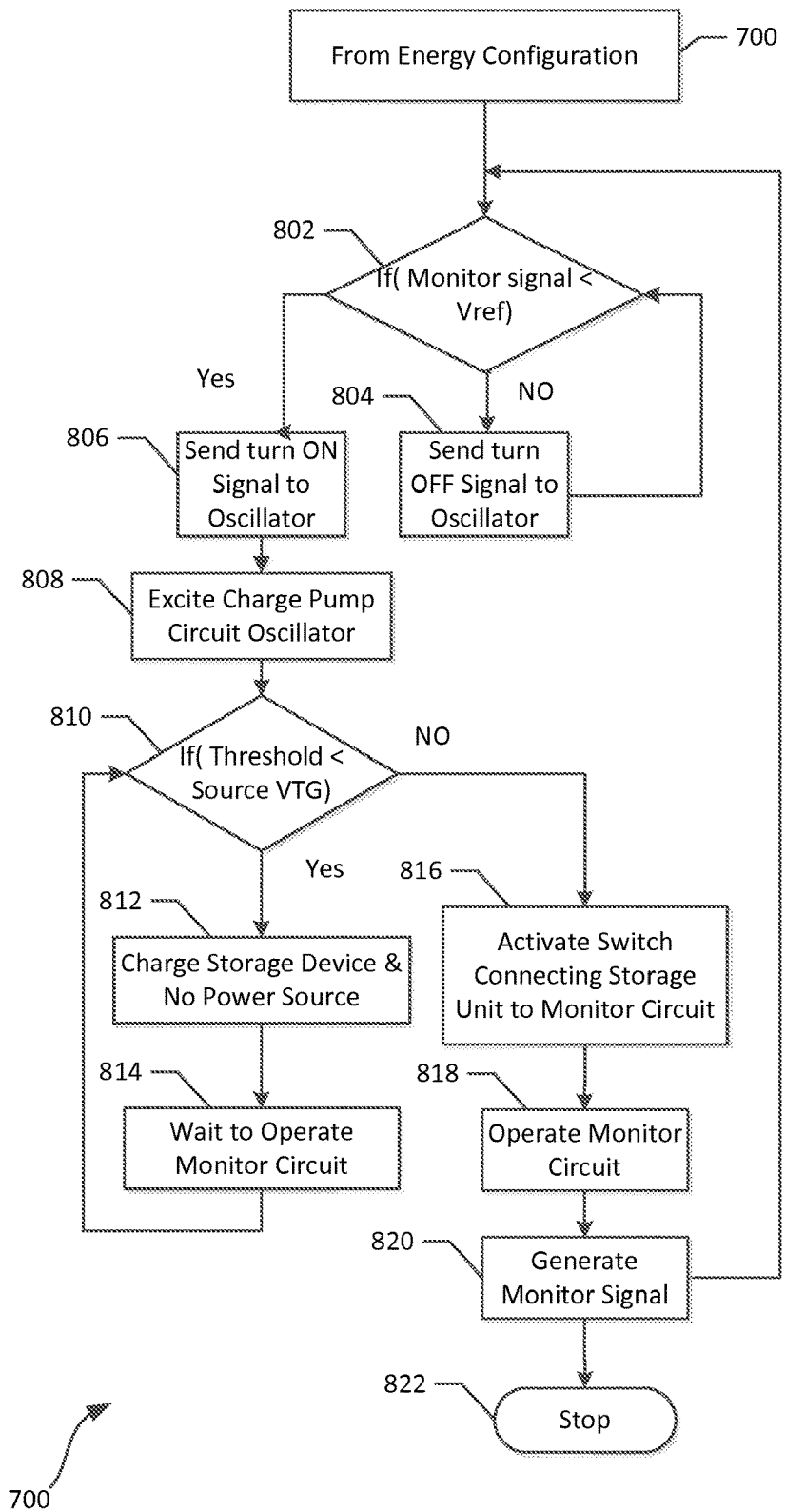
FIG. 11 is a flowchart of operation of the energy booster circuit of FIG. 9, according to an example embodiment.

Referring now to FIGS. 10-11, methods for configuring and operation of the energy booster circuit 600 and associated energy storage unit 608 are illustrated, according to an example embodiment. In FIG. 10, a method 700 is instantiated at a start operation 702, which indicates initial operation of the circuits and energy harvesters discussed herein. A user can initialize the circuits by providing one or more system requirements, such as the voltage and current levels, and a recharge cycle (step 704). Additionally, based on those voltage and current levels, the user can select a set of one or more energy sources (e.g., harvesters 302*a-e*) from which to receive energy, and based on expected energy levels to receive from particular harvesting techniques (step 706). Switches 306*a-e* can then be set according to the selected energy sources (step 708).

Following selection of particular energy sources, the user can configure the type of energy storage device in which the harvested energy is collected (step 710). If a battery is selected (step 712), a battery type is then selected (step 714). These can include selection of, for example, a lead acid battery (step 716) or a thin film rechargeable battery (step 718). If, when a storage device is selected, a capacitor is selected (step 720) or after a battery type is selected, a controller timer can be set to define a charging cycle of the storage element (step 722). This can include, for example, defining the amount of time between tests of the hose assembly 12, in a time in which there will reliably be sufficient charge collected in the storage device to allow for a test of an electrical property of the hose as well as to communicate that property to a remote receiver.

Once the controller settings are selected, an energy management control process can be performed (step 800), which generally corresponds to method 800 of FIG. 11.

Referring now to FIG. 11, a method of operation of the energy harvesting system of FIG. 6 is shown, and in particular relating to the switching timing in the energy booster circuit 600 of FIG. 8. The method 800 is instantiated by completion of the method 700 of FIG. 10, and occurs upon completed initialization of the circuit and installation of the hose assembly and associated hose monitoring system that includes the energy harvesting circuits as discussed herein.

From the configuration method 700, an assessment operation will determine whether a monitor signal received from the monitoring circuit 14 is lower than a reference signal (802). If the monitor signal is not lower than the reference signal, the circuit 600 will maintain an "off" signal transmitted to the oscillation circuit 606 (step 804). If the monitor signal has dropped below the reference signal, this indicates that the energy storage unit 608 should be recharged. Accordingly, comparator 618 will turn on the oscillation circuit 606 (step 806), and a charge pump circuit oscillator will initiate operation, thereby activating a charge pump (step 808). This will cause the circuit 600 to receive energy from one or more preconfigured energy harvesters 302*a-e*, as illustrated in FIG. 6.

If, during this charging process, a threshold voltage remains below a source voltage, the circuit will continue to charge the energy storage unit 608 (whether batteries 612 or capacitors 610) (step 810), and will ensure that the monitor circuit remains deactivated (steps 812, 814). This will continue until sufficient charge has built up in the energy storage unit 608. Once the storage threshold is met, MOSFET switch 616 is activated, connecting the storage unit 608 to the monitor circuit 14 (step 816). The monitor circuit can assess an electrical characteristic of the hose assembly and optionally communicate that characteristic to a remote receiver (step 818). The monitor circuit can also generate a monitor signal that can be assessed to determine a power level of the monitor circuit (i.e., to determine if the monitor circuit and associated energy storage unit 608 require recharging (step 820). If so, operation returns to step 802. Operation terminates at step 822, indicating completed use of the hose monitoring system Referring to FIGS. 1-11 overall, it is noted that a number of advantages are apparent in using the energy harvesting circuit and associated energy boot circuitry discussed herein. In particular, the circuits discussed provide an energy source that will not often require maintenance, since in many cases no batteries may be needed. Additionally, because existing environmental features of the hose assembly can be used in harvesting energy (e.g., expansion of the hose, increased temperature of the fluids within the hose, etc.), a reliable source of energy to be harvested is provided. Additionally, although a particular construction is illustrated herein, the energy harvesting unit can take a variety of forms, including a variety of different types of energy harvesting circuits, both including those illustrated herein and others as well.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A hose monitoring system comprising:
a hose assembly including a hose having a first conductive layer and a second conductive layer;
a monitoring circuit in electrical communication with the first and second conductive layers, the monitoring circuit configured to monitor hose degradation of the hose assembly by assessing an electrical characteristic of the hose assembly based on a voltage applied across the first conductive layer and the second conductive layer, the monitoring circuit configured to detect an electrical characteristic of the hose assembly; and
an energy harvesting unit in electrical communication with the monitoring circuit, the energy harvesting unit including one or more energy harvesters for providing electrical energy to the monitoring circuit, the one or more energy harvesters configured to generate electrical energy in response to a physical condition of the hose assembly and comprising at least one of a thermal sensor configured to generate energy in response to a temperature gradient between layers of the hose assembly, an electrostatic energy harvesting unit configured to collect static charges developed in the hose, or a piezoelectric energy harvesting unit configured to generate energy in response to stress applied to a piezo band extending around at least a portion of the hose.

2. The hose monitoring system of claim 1, further comprising an energy booster circuit electrically connected between the energy harvesting unit and the monitoring circuit.

3. The hose monitoring system of claim 2, further comprising a rechargeable energy storage unit electrically connected to the energy booster, the rechargeable energy storage unit configured to store energy received from the energy harvesting unit for use by the monitoring circuit.

4. The hose monitoring system of claim 3, wherein the rechargeable energy storage unit comprises a capacitor.

5. The hose monitoring system of claim 3, wherein the rechargeable energy storage unit comprises a battery.

6. The hose monitoring system of claim 1, wherein the monitoring circuit includes a communication module configured to provide wireless communication to a receiver positioned remotely from the monitoring circuit.

7. The hose monitoring system of claim 1, wherein the energy harvesting unit includes a plurality of energy harvesters of varying types.

8. The hose monitoring system of claim 1, wherein the monitoring circuit is electrically connected across a nipple and a socket of a hose assembly to respectively connect to the first and second conductive layers.

9. The hose monitoring system of claim 1, wherein the monitoring circuit is configured to periodically determine an electrical characteristic of the hose assembly and communicate the electrical characteristic to a receiver positioned remotely from the monitoring circuit.

10. A method of operating a hose monitoring system, the method comprising:
capturing energy via an energy harvesting unit associated with a hose assembly in response to a physical condition of the hose assembly, the hose assembly including a hose having a first conductive layer and a second conductive layer, the energy harvesting unit comprising at least one of a thermal sensor configured to generate energy in response to a temperature gradient between layers of the hose assembly, an electrostatic energy harvesting unit configured to collect static charges developed in the hose, or a piezoelectric energy harvesting unit configured to generate energy in response to stress applied to a piezo band extending around at least a portion of the hose;
providing the energy to a monitoring circuit in electrical communication with the first and second conductive layers the monitoring circuit configured to monitor hose degradation of the hose assembly; and
in response, assessing an electrical characteristic of the hose assembly via the monitoring circuit based on a voltage applied across the first conductive layer and the second conductive layer.

11. The method of claim 10, further comprising storing the energy captured by the energy harvesting unit in an energy storage unit.

12. The method of claim 10, further comprising enabling operation of an oscillator of an energy booster circuit electrically connected between the energy harvesting unit and the monitoring circuit, the oscillator enabling a charge pump configured to enable storage of energy in the energy storage unit.

13. The method of claim 10, further comprising delivering energy to the monitoring circuit from the energy storage unit.

14. The method of claim 10, wherein assessing an electrical characteristic of the hose assembly comprises applying the voltage across the first and second conductive layers to determine a resistance of the hose assembly.

15. The method of claim 10, wherein assessing the electrical characteristic of the hose assembly occurs periodically.

16. The method of claim 10, further comprising aggregating energy from a plurality of energy harvesting units, the plurality of energy harvesting units including at least first and second different types of energy harvesting units.

17. A hose monitoring system comprising:
a hose assembly including a hose having a first conductive layer and a second conductive layer;
a monitoring circuit in electrical communication with the first and second conductive layers the monitoring circuit configured to monitor hose degradation of the hose assembly by assessing an electrical characteristic of the hose assembly based on a voltage applied across the first conductive layer and the second conductive layer;
an energy harvesting unit including a plurality of energy harvesters the plurality of energy harvesters including an energy harvester configured to generate electrical energy in response to a physical condition of the hose assembly; and
an energy booster circuit including an energy storage unit and a charge pump, the energy booster circuit electrically connected between the energy harvesting unit and the monitoring circuit, the charge pump configured to enable storage of energy received from the energy harvesting unit in an energy storage unit, the energy storage unit electrically connected to the monitoring circuit and providing power to the monitoring circuit;
wherein the plurality of energy harvesters includes at least one of a thermal sensor configured to generate energy in response to a temperature gradient between layers of the hose assembly, an electrostatic energy harvesting unit configured to collect static charges developed in the hose, or a piezoelectric energy harvesting unit configured to generate energy in response to stress applied to a piezo band extending around at least a portion of the hose.

18. The hose monitoring system of claim 17, wherein the monitoring circuit includes a communication circuit configured to communicate with a remote monitor.

19. A hose assembly comprising:
a hose assembly including a hose having a first conductive layer and a second conductive layer;
a monitoring circuit in electrical communication with the first and second conductive layers, the monitoring circuit configured to monitor hose degradation of the hose assembly by assessing an electrical characteristic of the hose assembly based on a voltage applied across the first conductive layer and the second conductive layer; and
an energy harvesting unit including a thermal energy harvester integrated with the hose to generate an electrical signal based on a temperature gradient across the first and second conductive layers of the hose, the electrical signal connected to the monitoring circuit and used by the monitoring circuit to generate the voltage.

20. The hose assembly of claim 19, further comprising an energy booster circuit electrically connected to the energy harvesting unit and configured to collect harvested energy from the thermal energy harvester in an energy storage unit.

* * * * *